US005587377A

United States Patent [19]
Patel et al.

[11] Patent Number: 5,587,377
[45] Date of Patent: Dec. 24, 1996

[54] TERAZOSIN CRYSTALLINE POLYMORPH AND PHARMACEUTICAL COMPOSITIONS THEREOF

[75] Inventors: Mahendra R. Patel, East Brunswick; Kasireddy C. Reddy, New Brunswick; Pankaj J. Dave, Kendall Park, all of N.J.

[73] Assignee: Invamed, Inc., Dayton, N.J.

[21] Appl. No.: 547,209

[22] Filed: Oct. 24, 1995

[51] Int. Cl.⁶ .................... C07D 239/84; A61K 31/505
[52] U.S. Cl. ............................. 514/254; 544/291
[58] Field of Search ................. 544/291; 514/254

[56] References Cited

U.S. PATENT DOCUMENTS

| | | | |
|---|---|---|---|
| 4,026,894 | 5/1977 | Winn et al. | 260/256 |
| 4,112,097 | 9/1978 | Winn et al. | 424/251 |
| 4,251,532 | 2/1981 | Roteman | 424/251 |
| 4,816,455 | 3/1989 | Schickaneder et al. | 514/254 |
| 5,212,176 | 5/1993 | Kyncl et al. | 514/254 |
| 5,294,615 | 3/1994 | Meyer et al. | 514/254 |
| 5,362,730 | 11/1994 | Bauer et al. | 514/254 |
| 5,412,095 | 5/1995 | Morley et al. | 544/291 |
| 5,504,207 | 4/1996 | Mannino et al. | 544/291 |

FOREIGN PATENT DOCUMENTS 5-78352  3/1993  Japan .

*Primary Examiner*—Matthew V. Grumbling
*Attorney, Agent, or Firm*—Seidel, Gonda, Lavorgna & Monaco, P.C.

[57] ABSTRACT

The present invention relates to the discovery of novel polymorph form of an active pharmaceutical agent and the process for its preparation. More specifically, the present invention relates to the preparation of a novel polymorph form of terazosin hydrochloride, a well known anti-hypertensive agent.

3 Claims, 4 Drawing Sheets

TERAZOSIN CRYSTALLINE POLYMORPH AND PHARMACEUTICAL COMPOSITIONS THEREOF

FIELD OF THE INVENTION

The present invention relates to the discovery of a novel polymorph form of active pharmaceutical agent and processes for its preparation. More specifically, the present invention relates to the preparation of a novel polymorph form of terazosin hydrochloride, a well known anti-hypertensive agent.

BACKGROUND OF THE INVENTION

Polymorphic compounds, also known as allotrophic compounds, are compounds which can exist in two or more forms which although comprised of the same elemental components exhibit significantly different physical and chemical properties. The difference between the forms involves either a) the crystalline structure b) the number of atoms in the molecule of a gas, or c) the molecular structure of a liquid. Carbon for example, exists in several different polymorphic crystalline forms, diamond, carbon black and graphite.

Terazosin is chemically identified as 2-(4-(2-tetrahydrofuroyl)1-piperazine-1-yl)-4-amino-6, 7-dimethoxy quinazoline. This drug is used in the treatment of hypertension, benign prostatic hyperplasia and congestive heart failure. The drug is represented by the formula:

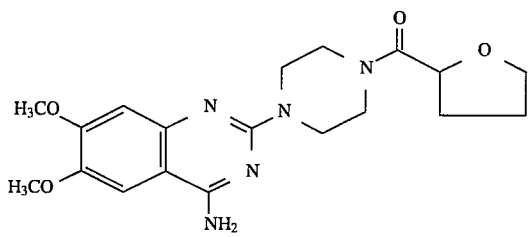

The method of preparation of 2(4-(2-tetrahydrofuroyl)-1-piperazine-1-yl)-4-amino-6, 7-dimethoxy quinazoline was first described and claimed in U.S. Pat. No. 4,026,894 to Winn et al. The compound synthesized by this method was identified and is referred to as the Form-I non-solvated crystalline polymorph. A pharmaceutically acceptable salt of terazosin is disclosed and claimed in U.S. Pat. No. 4,112,097, also to Winn et al.

The terazosin hydrochloride dihydrate salt and methods of preparation are disclosed in U.S. Pat. No. 4,251,532 to Roteman et al. The dihydrate form is allegedly more stable during storage in bulk form and more stable in solution and therefore more suitable for parenteral administration. U.S. Pat. No. 5,294,615 discloses the anhydrous non-solvated crystalline Form-II polymorph of terazosin hydrochloride, which is physically different from Form-I and allegedly has unexpectedly uniform bioavailability. The published Japanese Patent Application No. 5-78352 describes and claims a process of making a novel terazosin hydrochloride methanolate intermediate and the inter-conversions of the same to six-non-solvated crystalline polymorphs of terazosin hydrochloride.

U.S. Pat. No. 5,212,176 to Kyncl teaches the preparation of an enantiomeric excess of R(+) terazosin and its pharmaceutically acceptable salts. This enantiomer is disclosed as being useful in a variety of pharmaceutical dosage forms.

U.S. Pat. No. 5,412,095 to Morley et al. describes and claims processes for making a non-solvated crystalline terazosin polymorph Form-III and its methanolate intermediate. The methods for the conversion of the methanolate intermediate to the non-solvated crystalline polymorphs of terazosin involve using a variety of polar solvents such as ethanol/acetone for Form-I, ethanol for Form-II and dry acetone, ethanol, methylethylketone (2-butane) for Form-III in different experimental procedures. The methanolate intermediate is distinct from both the Form-I and Form-II intermediates which are easily isolated therefrom. Non-solvated terazosin hydrochloride Forms I, II, III and the dihydrate can be prepared using the methanolate intermediate. These compounds have been studied and distinguished using different instrumentation techniques such as x-ray diffraction, $C^{13}$ Nuclear Magnetic Resonance, (NMR) Fourier Transform Infrared spectrometry (FTIR) and Differential Scanning Calorimetry (DSC).

U.S. Pat. No. 5,362,730 to Bauer et al. discloses and claims a process for the preparation of terazosin monohydrochloride in which the dehydrate form or the anhydrous Form 1 terazosin hydrochloride is contacted with a polar organic solvent such as $C_1$–$C_6$ ketones or mixtures thereof. The anhydrous crystalline polymorph of terazosin monohydrochloride so produced is also claimed in a pharmaceutical composition.

The present invention comprises a novel polymorph form of terazosin hydrochloride monohydrate, Form IV and a process for its preparation without the need for the formation and isolation of an intermediate as required by the processes of the prior art.

SUMMARY OF THE INVENTION

Figure 1:
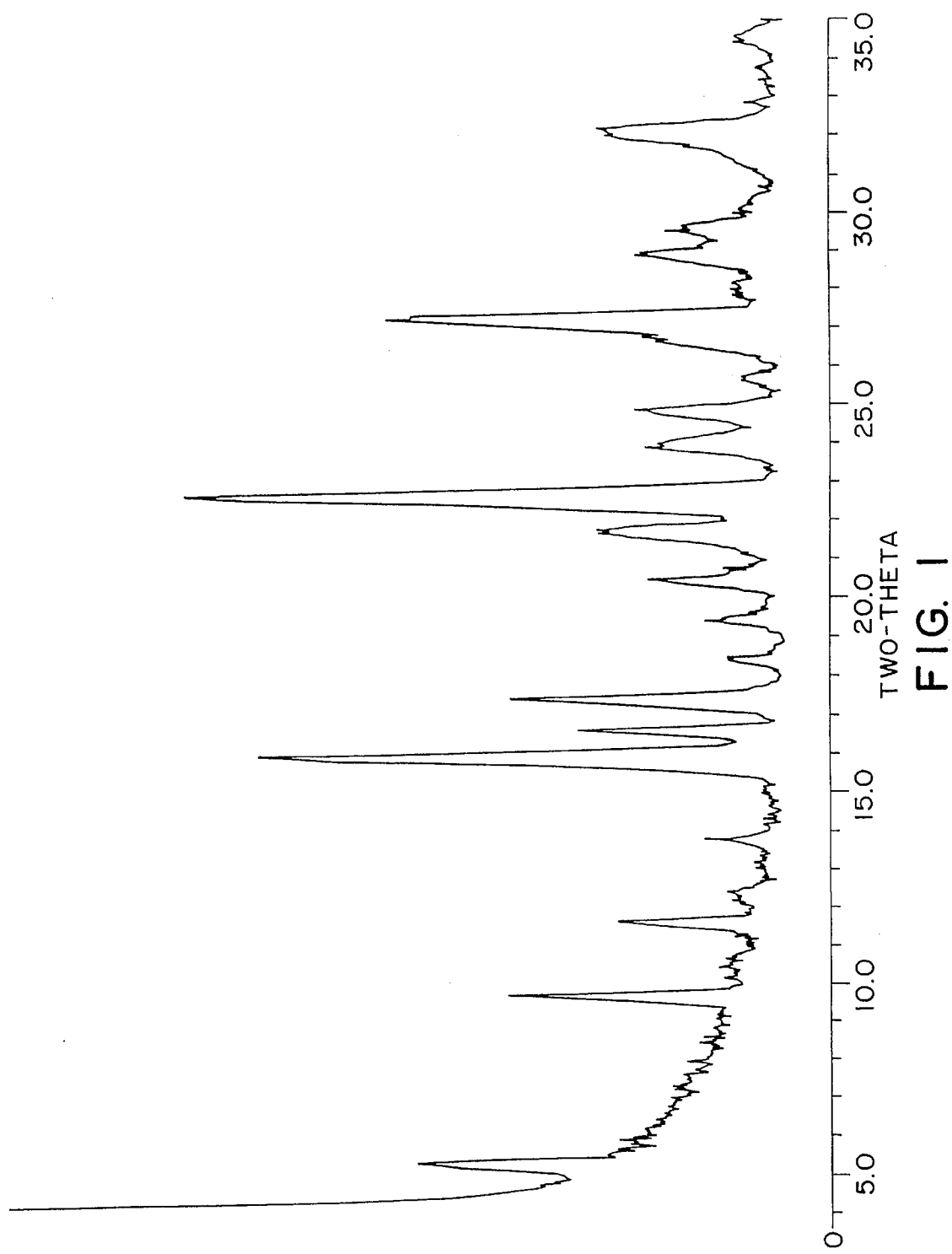
FIG. 1 is the powder x-ray diffraction pattern analysis of terazosin monohydrochloride monohydrate Form-IV.
Figure 2:
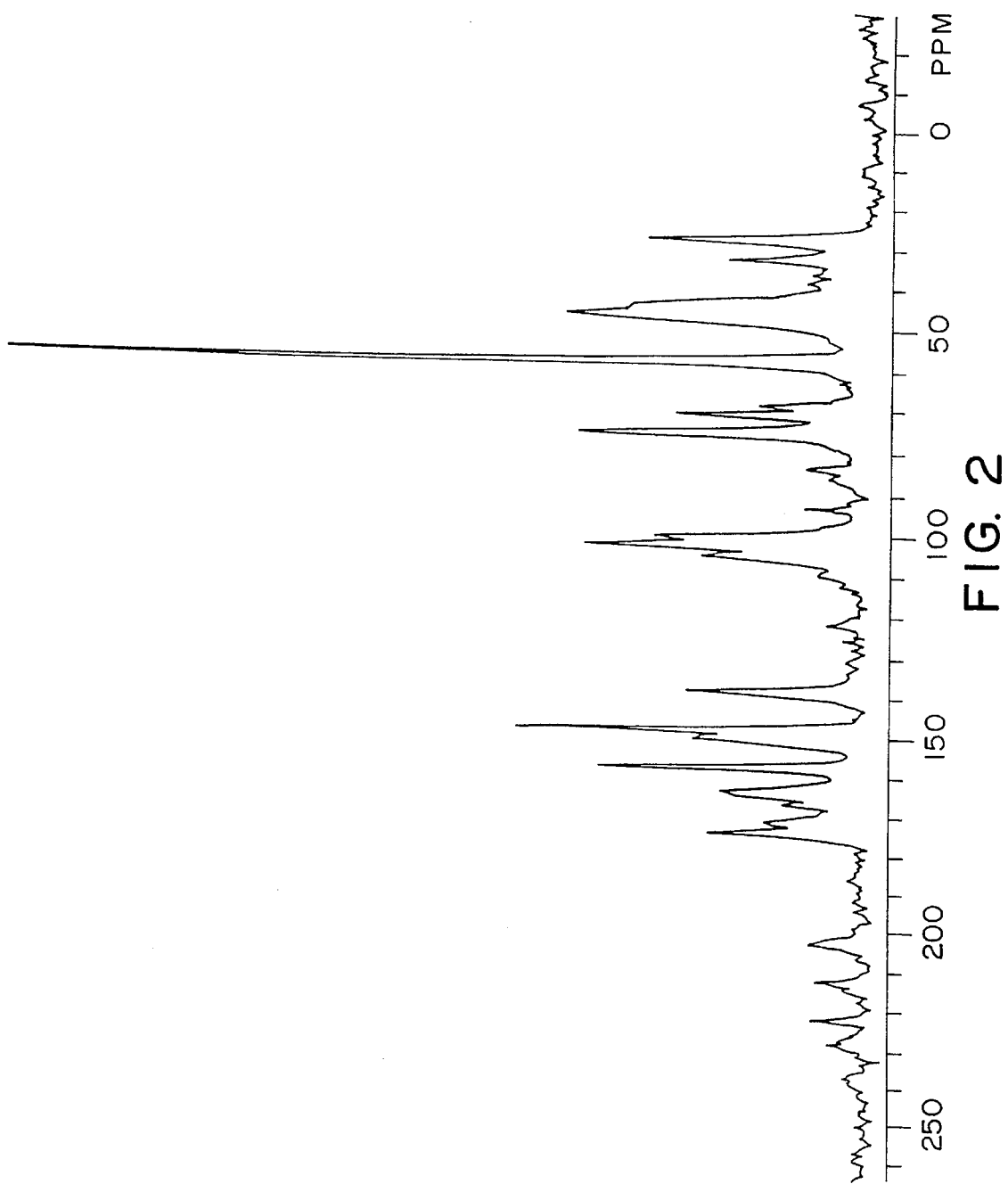
FIG. 2 is a $C^{13}$- NMR spectrum of terazosin monohydrochloride monohydrate Form-IV.
Figure 3:
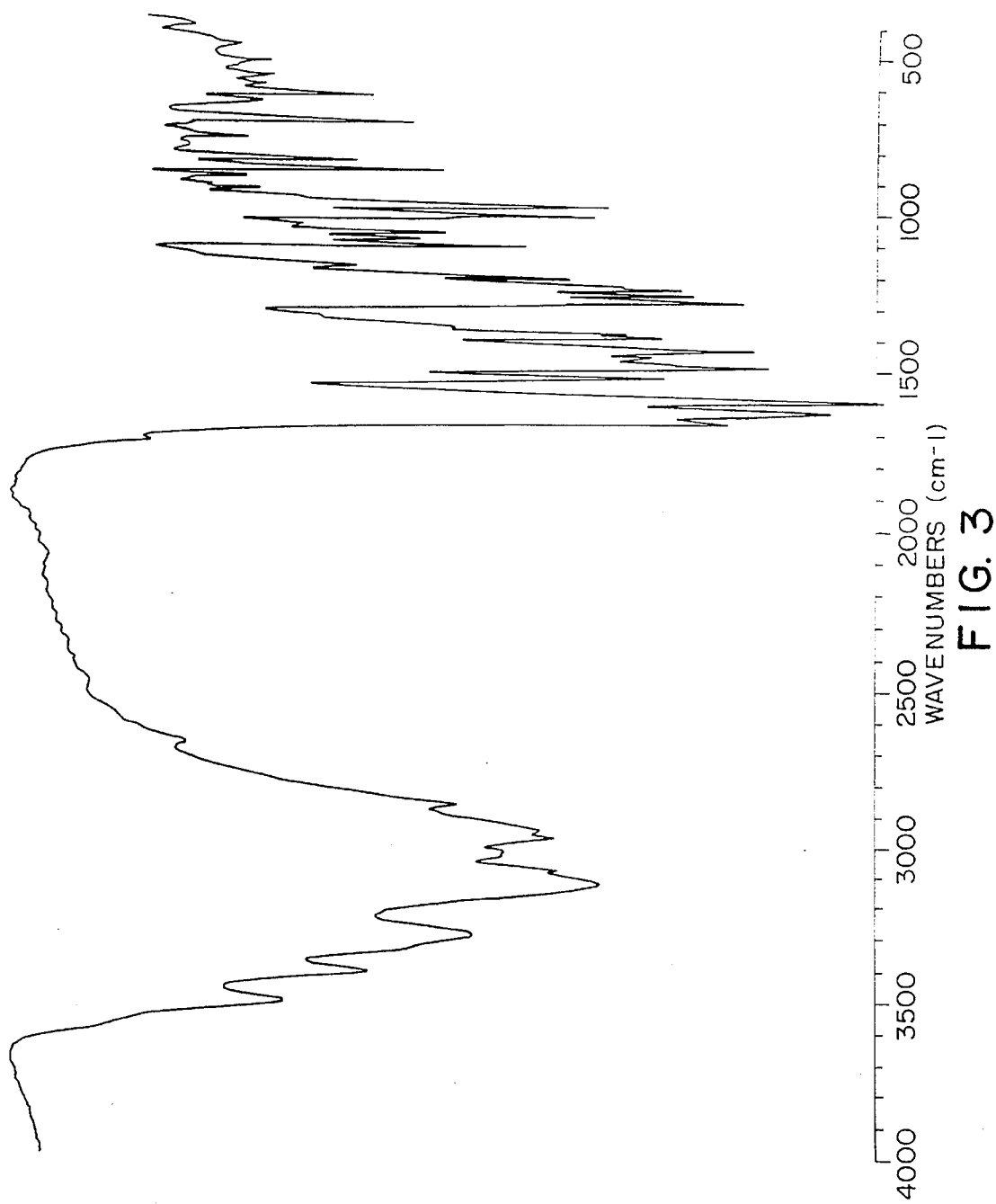
FIG. 3 is a Fourier transform infrared spectrum (FTIR) of terazosin monohydrochloride monohydrate Form-IV.
Figure 4:
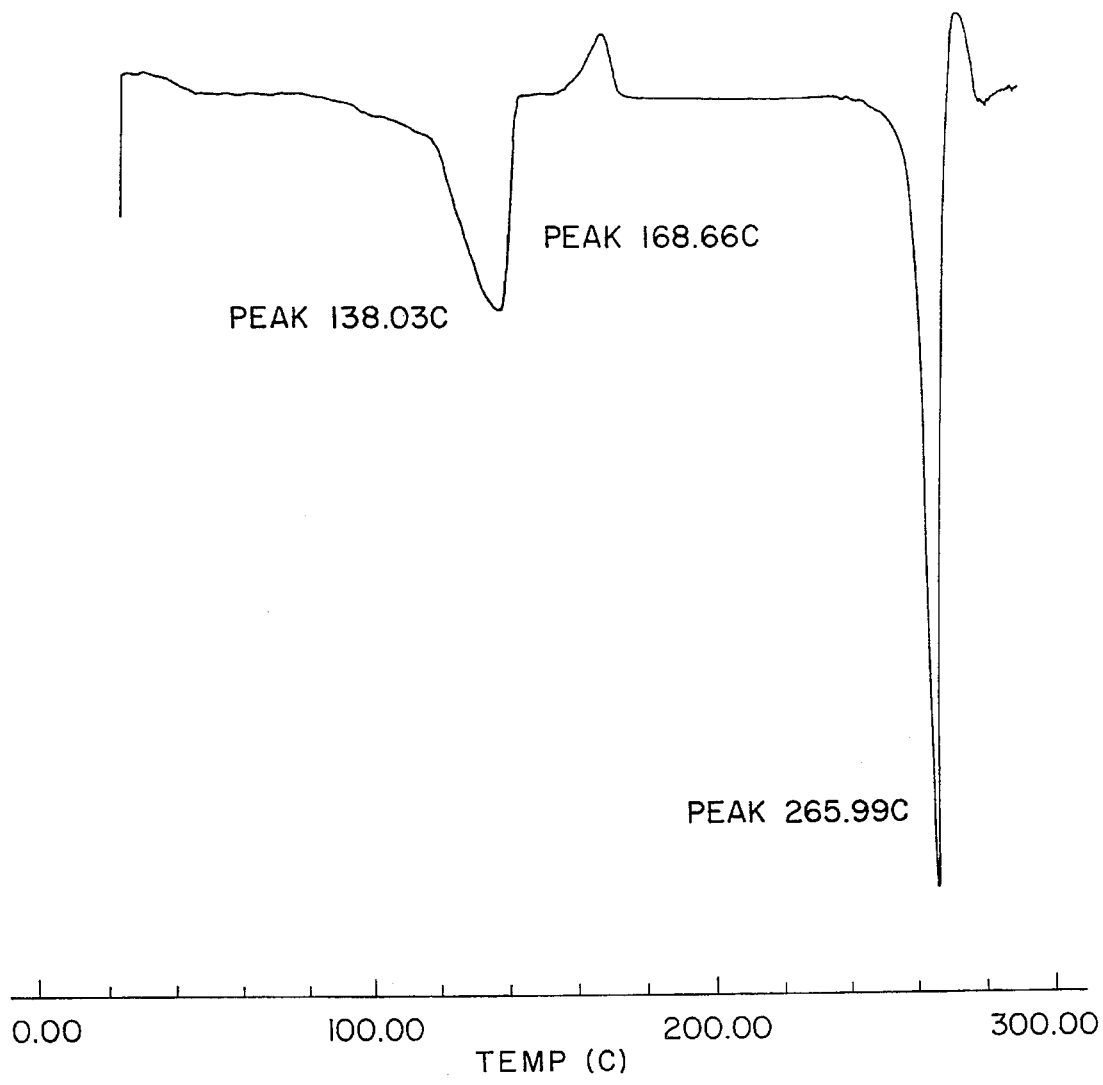
FIG. 4 is a differential scanning calorimetry thermogram (DSC) of terazosin monohydrochloride monohydrate Form-IV.

The present invention comprises a novel polymorph form of terazosin hydrochloride which will be designated as 1-(4-amino-6, 7-dimethoxy-2-quinazolinyl)-4-(2-tetrahydrofuroyl) piperazine monohydrochloride monohydrate Form-IV crystalline polymorph. This crystalline polymorph Form-IV compound is useful as an anti-hypertensive agent because of its superior solubility in water and improved stability to moisture during storage. It is a compound that can be easily prepared in greater purity and increased yields from its base. Additionally, the improved intermediate solubility of this polymorph form compared to the non-solvated and dihydrate polymorphs known in the prior art make it suitable for use in both oral tablets as well as readily prepared intravenous solutions.

DETAILED DESCRIPTION OF THE INVENTION

The compound of the present invention is prepared according to the following reaction scheme:

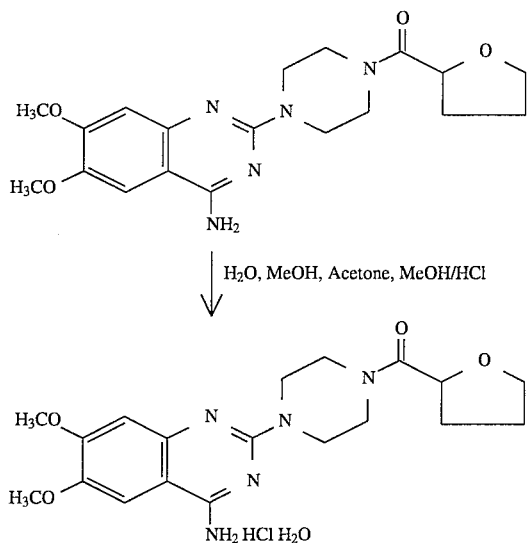

In the reaction illustrated above, the compound terazosin monohydrochloride monohydrate Form-IV was prepared by reacting from terazosin base 1-(4-amino-6, 7-dimethoxy-2-quinazolinyl)-4-(2-tetrahydrofuroyl) piperazine with methanolic HCl in water, methanol and acetone. The terazosin structure contains a primary amino group in the quinozoline ring. In general, bases are not very soluble in aqueous solutions for oral administration as therapeutic agents. Hence, most basic compounds must be converted to their corresponding hydrochloride salts in order to obtain the required solubility in aqueous solution.

In preparing hydrochloride salts of terazosin, several different alternative methods have been used in the prior art. The results of these alternative methods are described by the spectral data in the various patent documents discussed above.

The novel clathrate form of terazosin hydrochloride hydrate Form-IV is distinct from the Form-I, II &III non-solvated crystalline polymorphs of terazosin HCl as disclosed in the prior art. The hydrated monohydrochloride is prepared with terazosin base in the presence of water, methanol, methanolic HCl and acetone. Terazosin monohydrochloride hydrate has one mole of water of solvation per mole of terazosin hydrochloride in the crystalline solid. The existence of the monohydrate was confirmed with powder x-ray diffraction studies, $C^{13}$ NMR, FTIR and differential scanning calorimetry (DSC) thermograms (FIGS. 1–4). In the differential scanning thermogram (FIG. 4) the compound of the invention has an endotherm peak at 138.0° C. which is due to the loss of a water molecule from the crystal, and a smaller exotherm peak at 168.7° C. which is due to phase transition of the terazosin molecule itself.

The prior art terazosin monohydrochloride dihydrate compound exhibits a DSC thermogram pattern with an endotherm peak at 124.8° C., which is due to the loss of water molecules from the crystal. The difference in the endotherm peak of the hydrated clathrate Form-IV of the invention versus the dihydrate indicates that the water molecule of the terazosin monohydrochloride hydrate compound is more tightly bound within the crystalline structure of Form-IV. This increased water binding plays an important role in the stability of the compound. Additionally, terazosin hydrochloride monohydrate has superior compressibility compared to terazosin hydrochloride dihydrate. This property of terazosin hydrochloride monohydrate makes it more suitable for preparation of tablets using simple direct compression process.

The positions of the peaks in powder x-ray diffraction pattern studies at an angle of two theta (2θ) of terazosin HCl hydrate Form-IV are shown in FIG. 1 to be 5.24, 9.66, 11.55, 15.84, 16.58, 17.39, 19.41, 20.42, 21.67, 22.55, 23.90, 24.81, 26.70, 27.17, 28.86, 29.46, 29.63, 31.66 and 31.99. These values are unlike any of those shown in the prior art indicating a wholly novel compound. The thermogravimetric analysis of the monohydrate Form-IV exhibits a weight loss corresponding to the first endotherm on the DSC. This represents a 4.0% loss and again is due to the loss of water similar to that of terazosin monohydrochloride dihydrate which exhibited a weight loss of 7.7% in thermogravimetric analysis. The water content of Form-IV was found to be 4.4% using the Karl-Fisher method.

Also contemplated as falling within the scope of the present invention are pharmaceutical formulations comprising a therapeutically effective amount of the novel Form IV crystalline polymorph of terazosin hydrochloride of this invention in combination with a suitable pharmaceutically acceptable carrier. A preferred formulation in accordance with the invention comprises a unit dosage tablet form comprising the active terazosin hydrochloride compressed with tabletting agents and excipients known in the art.

In such solid dosage forms, the active compound is admixed with at least one inert diluent such as sucrose, lactose or starch. The oral dosage forms can also comprise, as is normal practice, additional substances other than inert diluents, e.g., lubricating agents such as magnesium stearate. The dosage forms may also comprise buffering agents. Tablets and pills can additionally be prepared for a sustained release or may be prepared with enteric coatings.

The following examples are set forth to define and teach methods and means to best practice the present invention. They are for illustrative purposes only and it is recognized that minor changes and variations may be made that are not specifically detailed therein. It is to be understood however, that to the extent that any such changes do not materially alter or change the process or the final product produced thereby, such change is contemplated as falling within the spirit and scope of the inventionas defined by the claims that follow.

EXAMPLE 1

Preparation of Terazosin HCl monohydrate Form-IV from Terazosin Base. 1.300 g (0.0033 mol) of terazosin base was suspended in 1.0 ml deionized water together with 15 mi. of methanol and 15 mi. of acetone. To this was added a methanolic hydrochloric acid solution in an amount sufficient to lower the solution to a pH of about 4.0–5.0. The solution and suspended solid was cooled down to 5°–10° C., the solid then filtered and dried at about 60° C. for 4.0 hr under vacuum. The process yielded 1.081g (88%) of terazosin HCl hydrate. (m.p.266°–267° C.)

Elemental analysis of the compound data showed
calcd.: C, 51.6; H, 6.3; N, 15.8; 0, 18.1
found: C, 51.3; H, 6.4; N, 15.8; 0, 17.9

EXAMPLE 2

Preparation of Terazosin HCl mononohydrate Form IV from Anhydrous Terazosin HCl.

2.002 g (0.0047 mol) of terazosin HCl anhydrous was added to 1.0 mL of deionized water and was stirred for about 10 mins. at room temperature until most of the solid was dissolved. To this was added 40 ml of methanol and 50 mL of acetone and this was stirred for 15 min at room temperature followed by cooling to 5°–10° C. with ice water. The solid was filtered and dried at 60° C. for 4 hr. under vacuum. The reaction yielded 1.820 g (88%) of terazosin hydrochloride monohydrate (m.p. 266° C.).

EXAMPLE 3

Solubility 2.0 g of terazosin HCl monohydrate Form-IV added into a 50 mL centrifuge tube. This tube was shaken for four minutes and filtered through a 0.50 μm nylon membrane filter. The resulting filtrate was serially diluted with water and the ultraviolet absorption maximum at 254 nm measured. The concentration of the dissolved terazosin was calculated from the absorption data from a standard concentration. The solubility is approx. 310 mg/mL.

EXAMPLE 4

Terazosin hydrochloride monohydrate (Form-IV) and terazosin hydrochloride dihydrate raw material samples were individually compressed using Laboratory Carver Press with prelubricated 9/32" round flat face beveledge embossed tooling. About 100 mg of the drug substance was weighed and compressed at various pressures. The hardness was measured by Schleuniger Tablet Hardness Tester.

|  | Hardness | |
| --- | --- | --- |
| Pressure Applied | Terazosin Hydrochloride monohydrate | Terazosin hydrochloride dihydrate |
| 0.5 ton | 11.0 Sc | 4.5 Sc |
| 0.7 ton | 12.3 Sc | 5.4 Sc |
| 1.0 ton | 13.7 Sc | 7.4 Sc |

EXAMPLE 5

Moisture Stability

About 100 mg of Terazosin hydrochloride monohydrate (Form IV) and Terazosin hydrochloride dihydrate raw material samples were stored at 40° C./75 % RH and the change in water content was monitored by weight.

| Terazosin hydrochloride monohydrate | |
| --- | --- |
| Time | Change in water content |
| 1 week | −0.12% |
| 2 weeks | −0.12% |
| 3 weeks | −0.00% |
| 4 weeks | −0.72% |

| Terazosin hydrochloride dihydrate | |
| --- | --- |
| Time | Change in water content |
| 1 week | −0.1% |
| 2 weeks | −0.2% |
| 3 weeks | −0.9% |
| 4 weeks | −1.42% |

What we claimed is:

1. A novel crystalline polymorph 1-(4-amino-6, 7-dimethoxy-2-quinazolinyl-4-(tetrahydrofuroyl) piperazine monohydrochloride monohydrate Form-IV, characterized by peaks in the powder X-ray diffraction pattern at values of two theta of 5.24±0.2, 9.66±0.2, 11.55±0.2, 15.84±0.2, 16.58 ±0.2, 17.39±0.2, 19.41±0.2, 20.42±0.2, 21.67±0.2, 22.55±0.2, 23.90 ±0.2, 24.81±0.2, 26.70±0.2, 27.17±0.2, 28.86±0.2, 29.46±0.2, 31.66 ±0.2, 31.99±0.2.

2. A solid pharmaceutical dosage form comprising the novel crystalline polymorph of claim 1 formulated in a pharmaceutically acceptable solid carrier.

3. A method for the treatment of hypertension comprising the oral administration of the pharmaceutical dosage form of claim 2.

\* \* \* \* \*